United States Patent
Tanaka et al.

(10) Patent No.: US 8,372,070 B2
(45) Date of Patent: Feb. 12, 2013

(54) SURGICAL SYSTEM AND SURGICAL OPERATION METHOD

(75) Inventors: Kazue Tanaka, Sagamihara (JP); Satoshi Honda, Hachioji (JP); Hideo Sanai, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 801 days.

(21) Appl. No.: 12/146,908

(22) Filed: Jun. 26, 2008

(65) Prior Publication Data

US 2009/0326569 A1    Dec. 31, 2009

(51) Int. Cl.
    *A61B 17/32* (2006.01)
(52) U.S. Cl. .......................................... 606/42; 606/169
(58) Field of Classification Search .................. 606/167, 606/169–171, 1, 32, 37, 4, 45, 792; 600/562, 600/564, 118
    See application file for complete search history.

(56) References Cited

U.S. PATENT DOCUMENTS

| 4,931,047 A | 6/1990 | Broadwin et al. |
| 2005/0020967 A1* | 1/2005 | Ono .............................. 606/169 |
| 2006/0270916 A1 | 11/2006 | Skwarek et al. |
| 2007/0016235 A1* | 1/2007 | Tanaka et al. .................. 606/169 |
| 2007/0055277 A1* | 3/2007 | Osorio et al. .................... 606/92 |
| 2008/0058803 A1* | 3/2008 | Kimura ............................ 606/49 |

FOREIGN PATENT DOCUMENTS

| JP | 07-047080 | 2/1995 |
| JP | 10-094545 | 4/1998 |
| JP | 10-225462 | 8/1998 |
| JP | 2000-271145 | 10/2000 |
| JP | 2002-306507 | 10/2002 |
| WO | WO 2005/048809 A1 | 6/2005 |

* cited by examiner

*Primary Examiner* — Kathleen Sonnett
*Assistant Examiner* — Sarah W Aleman
(74) *Attorney, Agent, or Firm* — Scully, Scott, Murphy & Presser, P.C.

(57) ABSTRACT

A surgical system includes a surgical instrument including a conducting section transmitting ultrasound vibration generated by an ultrasound transducer to a distal end portion and transmitting a high-frequency output signal to the distal end portion, an ultrasound drive section outputting an ultrasound drive signal to the ultrasound transducer, a high-frequency output section outputting a high-frequency output signal to the conducting section, a detection section detecting an ultrasound impedance of a surgical site to which ultrasound energy and high-frequency energy are provided from the distal end portion by outputting both signals simultaneously to the surgical instrument, a determination section determining whether the detected ultrasound impedance is in a predetermined range, and a control section performing control to increase a high-frequency output value by a first predetermined amount or decrease the high-frequency output value by a second predetermined amount when the detected ultrasound impedance is out of the predetermined range.

18 Claims, 10 Drawing Sheets

| US impedance (Ω) \ HF OUTPUT (W) | 10 | 20 | 30 | 40 | 50 | 60 | 70 |
|---|---|---|---|---|---|---|---|
| 100 | -1 | -1 | -2 | -5 | -10 | -10 | 0 |
| 150 | -1 | -1 | -1 | -2 | -5 | -5 | 0 |
| 200 | -1 | -1 | -1 | -2 | -2 | -2 | 0 |
| 800 | 2 | 1 | 1 | 1 | 1 | 1 | 0 |
| 900 | 5 | 2 | 2 | 2 | 2 | 2 | 0 |
| 1000 | 10 | 5 | 5 | 5 | 5 | 2 | 0 |
| 1100 OR MORE | 10 | 10 | 5 | 5 | 5 | 5 | 0 |

| US impedance (Ω) \ HF OUTPUT (W) | 10 | 20 | 30 | 40 | 50 | 60 | 70 |
|---|---|---|---|---|---|---|---|
| 100 | -1 | -1 | -2 | -5 | -10 | -10 | 0 |
| 200 | 0 | 0 | -1 | -2 | -5 | -5 | 0 |
| 300 | 0 | 0 | 0 | 0 | 0 | 0 | 0 |
| 400 | 0 | 0 | 0 | 0 | 0 | 0 | 0 |
| 500 | 0 | 0 | 0 | 0 | 0 | 0 | 0 |
| 600 | 2 | 1 | 1 | 1 | 1 | 1 | 0 |
| 700 | 5 | 2 | 2 | 2 | 2 | 2 | 0 |
| 800 | 10 | 5 | 5 | 5 | 5 | 2 | 0 |
| 900 | 10 | 10 | 5 | 5 | 5 | 5 | 0 |
| 1000 | 10 | 10 | 10 | 5 | 5 | 5 | 0 |
| 1100 OR MORE | 10 | 10 | 10 | 10 | 5 | 5 | 0 |

SURGICAL SYSTEM AND SURGICAL OPERATION METHOD

BACKGROUND OF THE INVENTION

1. Field of the Invention

The present invention relates to a surgical system and a surgical operation method for performing a surgical operation using an ultrasound coagulating and dissection device and a high-frequency cautery.

2. Description of the Related Art

Ultrasound coagulating and dissection devices (ultrasound drive devices) which enable dissection treatment to be performed while coagulating living biological tissue or an organ under surgery by using ultrasound energy and high-frequency cauteries (high-frequency output devices or electrosurgical scalpels) which pass high-frequency energy through living biological tissue or an organ to perform cauterization are widely used in surgery in these years.

For example, Japanese Patent Application Laid-Open Publication No. 10-225462 discloses a surgical system in which an ultrasound coagulating and dissection device and an electrosurgical scalpel are used at the same time.

According to the example of the related art, an ultrasound transducer is contained in a pair of electrodes of a bipolar treatment instrument that performs treatment using a high-frequency electric power (high-frequency output). The ultrasound transducer is driven by a control circuit.

The control circuit includes a driving unit that drives the ultrasound transducer to produce ultrasound, an amplitude detection section for detecting an amplitude of ultrasound vibration) a signal processor performing amplification and processing of a signal the amplitude of which is detected by the amplitude detection section, and a main controller controlling the entire system.

When the electrosurgical scalpel is used to perform treatment such as coagulation hemostasis of living biological tissue, the main controller automatically controls turning on and off of high-frequency output in accordance with an acoustic impedance of the living biological tissue caused in the process of cauterization of the living biological tissue between the pair of electrodes of the bipolar treatment instrument.

The acoustic impedance is detected from the amplitude of ultrasound from the ultrasound transducer and is compared with a threshold to automatically control turning on and off of high-frequency power.

The example of the related art also describes the following operation.

When the electrosurgical scalpel is used to perform treatment such as coagulation hemostasis of living biological tissue, a cauterized region is hardened and the acoustic impedance of the region increases during the process of cauterization of the living biological tissue between the electrode pair of the bipolar treatment instrument.

On the other hand, immediately before the start of cauterization, the acoustic impedance of the living biological tissue is low. Therefore, the acoustic impedance is detected from the amplitude of ultrasound from the ultrasound transducer and is compared with the threshold to automatically control turning on and off of high-frequency power.

It is also described that the treatment is performed safely and reliably by automatically controlling turning on and off of high-frequency power while the state of cauterization (of the living biological tissue under treatment) is being acoustically monitored, rather than relying on the visibility of visual checking of the living biological tissue (body region) under treatment.

SUMMARY OF THE INVENTION

A surgical system according to the present invention includes:

a surgical instrument including a conducting section transmitting ultrasound vibration generated by an ultrasound transducer to a distal end portion that functions as a treatment section and transmitting a high-frequency output signal to the distal end portion;

an ultrasound drive section outputting an ultrasound drive signal for driving the ultrasound transducer;

a high-frequency output section outputting a high-frequency output signal to the conducting section;

a detection section detecting an ultrasound impedance corresponding to an ultrasound drive state of the distal end portion in a state in which the ultrasound drive signal and the high-frequency output signal are being outputted to the surgical instrument to provide ultrasound energy and high-frequency energy from the distal end portion to a site of surgery;

a determination section determining whether the ultrasound impedance value detected by the detection section is within a predetermined range; and a control section performing control to increase the high-frequency output value by a first predetermined amount or to decrease the high-frequency output value by a second predetermined amount when the determination section determines that the ultrasound impedance value is out of the predetermined range.

A surgical operation method for performing a surgical operation by using a surgical instrument including a conducting section transmitting ultrasound vibration generated by an ultrasound transducer to a distal end portion that functions as a treatment section and transmitting a high-frequency output signal to the distal end portion according to the present invention, the method includes the steps of:

detecting an ultrasound impedance corresponding to an ultrasound drive state of the distal end portion in a state in which ultrasound energy and high-frequency energy are provided from the distal end portion to a site of surgery by driving the ultrasound transducer by an ultrasound drive signal and by outputting a high-frequency output signal to the conducting section;

determining whether an ultrasound impedance value detected by the step of detecting is in a predetermined range; and performing control to increase the high-frequency output value by a first predetermined amount or to decrease the high-frequency output value by a second predetermined amount when the step of determining determines that the ultrasound impedance value is out of the predetermined range.

DETAILED DESCRIPTION OF THE PREFERRED EMBODIMENTS

Embodiments of the present invention will be described with reference to the accompanying drawings.

First Embodiment

A first embodiment of the present invention will be described with reference to FIGS. 1 to 7. An object of the present embodiment is to provide a surgical system and a surgical operation method that enable living biological tissue under surgery to be removed efficiently in a short period of time. In particular, an object of the present embodiment is to provide a surgical system and a surgical operation method that enable living biological tissue under surgery to be removed efficiently in a short period of time by reducing the trouble of adjusting a high-frequency output (controlling a high-frequency output value) during dissection treatment.

Figure 1:
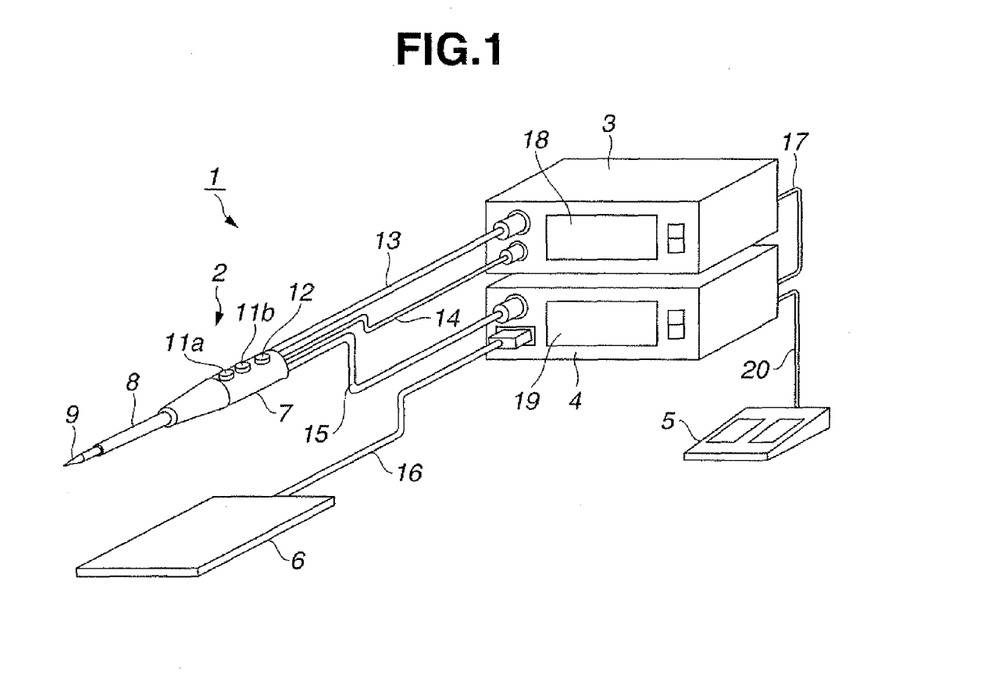
FIG. 1 is a perspective view showing a general configuration of a surgical system according to a first embodiment of the present invention.

FIG. 1 shows a general configuration of a surgical system 1 according to the first embodiment of the present invention. As shown in FIG. 1, the surgical system 1 includes a handpiece 2 as a surgical treatment instrument for performing treatment such as dissection of living biological tissue to be treated.

The surgical system 1 includes an ultrasound coagulating and dissection device main unit 3 (simply referred to as an ultrasound drive device) that provides an ultrasound drive signal for driving an ultrasound transducer (see FIG. 2) contained in the handpiece 2 and a high-frequency cautery main unit 4 (simply referred to as a high-frequency output device) that provides a high-frequency output (high-frequency current) to the handpiece 2.

The surgical system 1 includes a foot switch 5 for instructing to turn on and off the high-frequency output and a counter electrode plate 6 for forming a return circuit for the high-frequency output.

The handpiece 2 includes a grasping section 7 grasped by an operator and a shaft 8 projecting forward from the grasping section 7. A treatment section 9 shaped like a spatula for performing treatment such as dissection is provided at the distal end portion of the shaft 8.

Provided on the grasping section 7 are a dissection selection switch 11a and a coagulation selection switch 11b as selection switches for making a selection in treatment by the treatment section 9. An operation switch 12 (or a start switch) is also provided on the grasping section 7 for tentatively outputting an ultrasound and high-frequency power.

Extended from the rear end of the grasping section 7 of the handpiece 2 are an ultrasound drive cable 13, a hand switch cable 14, and a high-frequency output cable 15. Connecters at ends of the ultrasound drive cable 13 and the hand switch cable 14 are detachably connected to the ultrasound drive device 3.

A connecter at the rear end of the high-frequency output cable 15 is detachably connected to the high-frequency output device 4.

A connector at an end of a counter electrode plate cable 16 connected to the counter electrode plate 6 is also detachably connected to the high-frequency output device 4. The counter electrode plate 6 is disposed on a body part such as buttocks of a patient so as to come into contact with a wide area of the body part.

The ultrasound drive device 3 and the high-frequency output device 4 are interconnected through a communication cable 17 as shown in FIG. 1 so that the ultrasound drive device 3 and the high-frequency output device 4 can bi-directionally transmit and receive signals.

Front panels 18, 19 are provided for example on the front of the ultrasound drive device 3 and the high-frequency output device 4 for performing various operations and presenting a display.

The foot switch 5 is connected to the high-frequency output device 4 through a foot switch cable 20.

Figure 2:
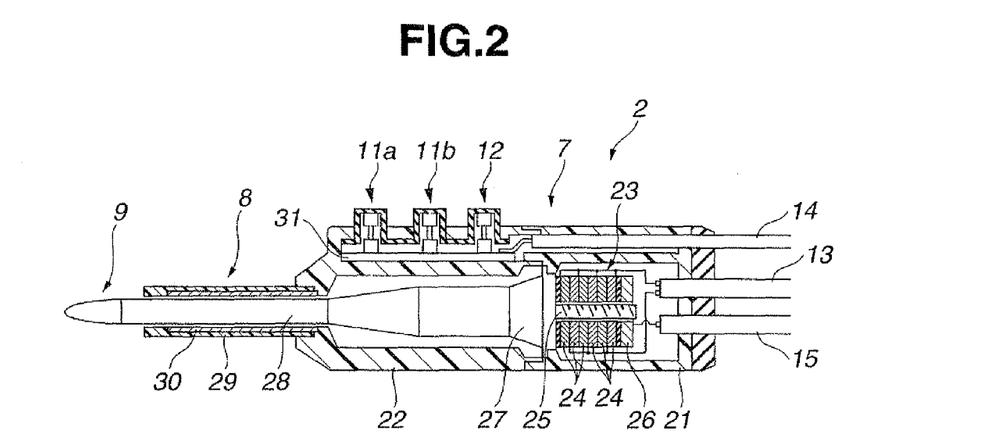
FIG. 2 is a cross-sectional view showing an internal configuration of a handpiece.

FIG. 2 shows an internal structure of the handpiece 2. In the handpiece 2, a substantially cylindrical main case 21, which forms the grasping section 7, and a sub case 22 connected to the front end of the main case 21 form a housing. An ultrasound transducer 23 connected to the ultrasound drive cable 13 is provided inside the main case 21.

In the ultrasound transducer 23, multiple ring-shaped electrostriction elements 24 are stacked in layers and fixed by a bolt 25 and a nut 26 in such a manner that they are jointed together. An ultrasound drive signal is applied to electrodes provided at surfaces to cause ultrasound vibration of the multiple electrostriction elements 24.

The ultrasound vibration is transmitted to the treatment section 9 at the distal end portion through a horn 27 and a probe 28 coupled to the front end of the bolt 25.

The metal nut 26 forms a conducting section to which a conducting wire of the high-frequency output cable 15 is connected. When a high-frequency output signal is applied to the nut 26, the signal is transmitted to the treatment section 9 at the distal end portion through the metal bolt 25 and the metal probe 28.

In this situation, when the treatment section 9 comes into contact with an organ to be treated, a high-frequency output signal (high-frequency current) flows from the contact portion to the organ as high-frequency energy. The high-frequency output signal transmitted to the organ returns to the high-frequency output device 4 through the counter electrode plate 6 and the counter electrode plate cable 16 which form a return path.

The probe 28 is inserted in a metal pipe 30 covered with an insulating pipe 29 as shown in FIG. 2.

Multiple signal lines inserted in the hand switch cable 14 are connected to a circuit board 31 and then connected to switching elements which are provided on the circuit board 31 and form the dissection selection switch 11a, the coagulation selection switch 11b, and the operation switch 12 covered with a rubber cover. Each of the switching elements can be turned on and off by pressing down a portion of the rubber cover.

Figure 3:
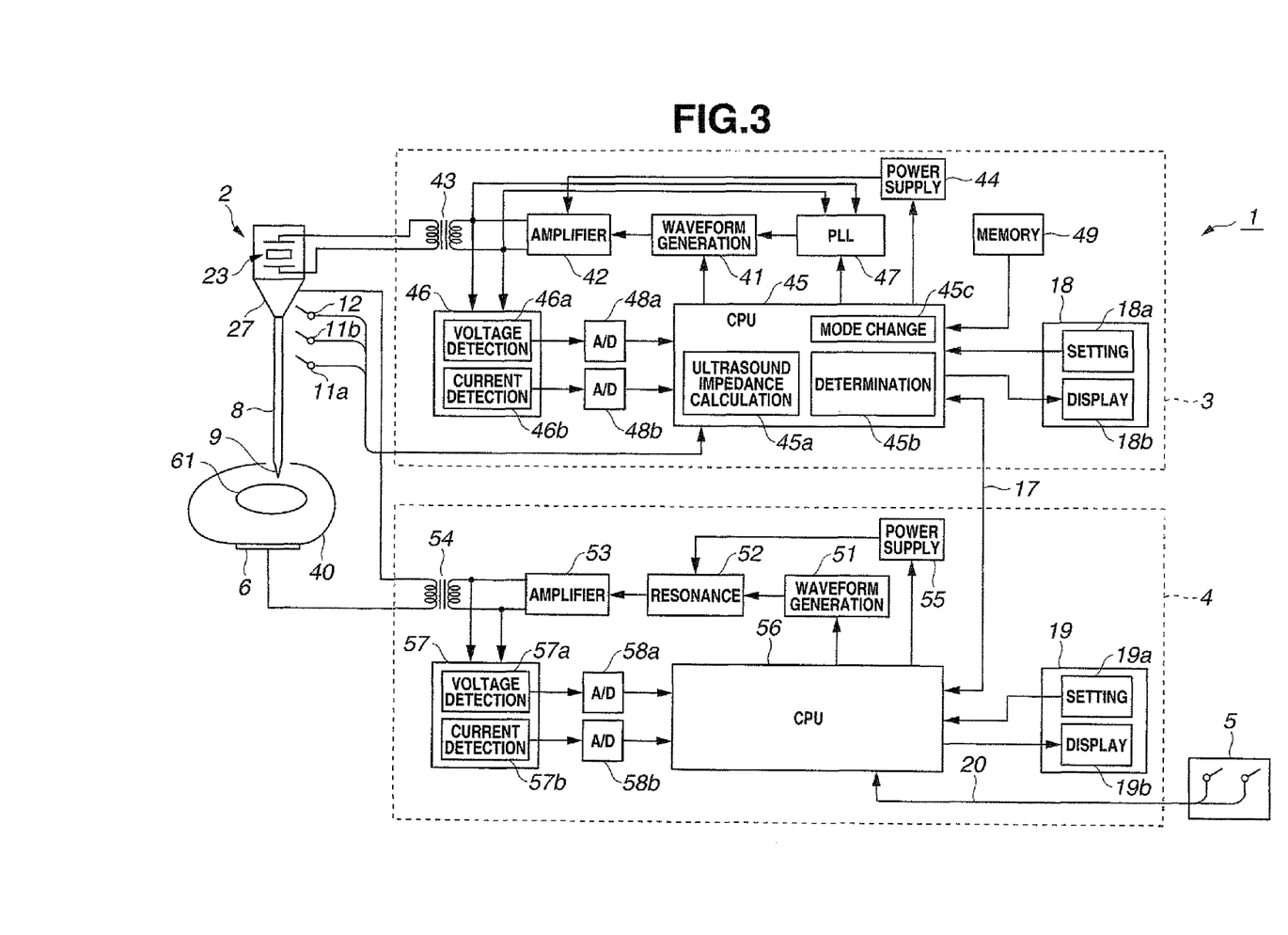
FIG. 3 is a block diagram showing a detailed configuration of the surgical system.

FIG. 3 shows a detailed configuration of the surgical system 1 shown in FIG. 1. The ultrasound drive device 3 contains a waveform generation circuit 41 which generates a sinusoidal signal, for example. The sinusoidal signal outputted from the waveform generation circuit 41 is amplified by an amplifier 42 and is then applied to a primary winding of an output transformer 43. The sinusoidal signal is then applied from an output terminal of a secondary winding of the output transformer 43 to the ultrasound transducer 23 in the handpiece 2 as an ultrasound drive signal.

The amplitude of the ultrasound drive signal, that is, ultrasound outputted from the ultrasound transducer 23, is adjusted according to a power supply voltage provided from a voltage-variable power supply circuit 44 to the amplifier 42. The power supply voltage of the power supply circuit 44, that is, ultrasound outputted, and operation of the waveform generation circuit 41 are controlled by a central processing unit (CPU) 45.

The CPU 45 controls an output voltage of the power supply circuit 44 in accordance with a setting operation performed in a setting section 18a on the front panel 18 so that an ultrasound output value according to the setting operation can be achieved. A display 18b is provided on the front panel 18 for displaying information such as an ultrasound output value outputted from the CPU 45.

The sinusoidal signal amplified by the amplifier 42 is inputted into a current detection circuit 46a and a voltage detection circuit 46b that form a detection circuit 46. The sinusoidal signal is also inputted into a PLL circuit 47.

The PLL circuit 47 performs PLL control to drive the ultrasound transducer 23 with an ultrasound drive signal having a resonance frequency appropriate to the ultrasound transducer 23. The PLL circuit 47 controls the ultrasound transducer 23 so that the voltage and current in the ultrasound drive signal is in phase with each other. The operation of the PLL circuit 47 is controlled by the CPU 45.

The current detection circuit 46a and the voltage detection circuit 46b detect the sinusoidal signal amplified by the amplifier 42 and convert the sinusoidal signal to a direct current (DC) signals representing effective values. The DC voltage and current values are converted to digital voltage and current by A/D conversion circuits 48a, 48b at predetermined intervals, for example every 10 ms, and the digital voltage and current are inputted in the CPU 45.

The CPU 45 uses the inputted DC voltage and current values to calculate an ultrasound output value and also calculate (detect) an ultrasound output impedance by taking into account the state of load placed when the ultrasound transducer 23 is driven (in particular, the sate in which ultrasound energy from the treatment section 9 is being applied to living biological tissue to be cut).

That is, the CPU 45 has a function of an ultrasound impedance calculation section (or detection section) 45a, which forms a monitor section that monitors ultrasound impedance.

The CPU 45 makes determination as to whether the calculated ultrasound impedance value is within a predetermined ultrasound impedance range suitable for performing treatment in a state of dissection treatment by the treatment section 9 at the distal end portion of the handpiece 2, in particular, in a treatment state in which the operator performs dissection treatment by dissection and coagulation while moving the treatment section 9 at a predetermined speed. That is, the CPU 45 has a function of a (ultrasound impedance range) determination section 45b. The CPU 45 also has a function of mode change (or waveform change) 45c as will be described later with reference to FIG. 8.

The information indicating the predetermined ultrasound impedance range suitable for the dissection treatment state has been stored in a memory 49, for example. The CPU 45 refers to the information in making the determination.

When the CPU 45 determines that the calculated ultrasound impedance value is within the predetermined ultrasound impedance range suitable for the dissection treatment state, the CPU 45 performs control to maintain the high-frequency output value without changing the high-frequency output.

On the other hand, when the CPU 45 determines that the calculated ultrasound impedance value is out of the predetermined range, the CPU 45 performs control to change the high-frequency output (from the high-frequency output value at that point of time).

When performing control to change the high-frequency output value, the CPU 45 changes the high-frequency output value so that the ultrasound impedance value approaches the predetermined ultrasound impedance range suitable for the dissection treatment state, according to whether the determination is that the ultrasound impedance value is greater than or equal to the upper limit of the predetermined ultrasound impedance range or that the ultrasound impedance is less than or equal to the lower limit of the range.

In particular, when the determination is that the value is greater than or equal to the upper limit, it means that site of dissection (organ or living biological tissue) is dry or hard (in ultrasound-treatment terms). Therefore the CPU 45 performs control to increase the high-frequency energy to increase the dissection capability of the high-frequency energy. As the high-frequency energy increases, the amount of water vapor generated by the high-frequency energy increases and the ultrasound impedance value decreases.

On the other hand, when the determination is that the value is lower than or equal to the lower limit, the site of dissection (organ or living biological tissue) is in a state opposite the state described above. Therefore the CPU 45 performs control to decrease the high-frequency output value so as to reduce the dissection capability.

When the dissection is performed at the decreased high-frequency value, sufficiently high coagulation (hemostasis) performance can also be achieved. Accordingly, a proper dissection treatment state in which both the dissection function and the coagulating function are in balance is approached. The control also increases the ultrasound impedance value as compared with the value before the reduction of the high-frequency output value.

The control described above forms a control loop such that the ultrasound impedance value corresponding to an ultrasound drive state when dissection treatment is performed by the treatment section 9 to which the ultrasound is transmitted from the ultrasound transducer 23 falls within the predetermined impedance range suitable for the dissection treatment state.

As shown in FIG. 3, an instruction signal generated by a switch operation of the dissection selection switch 11a, the coagulation selection switch 11b, or the operation switch 12 is inputted into the CPU 45. The CPU 45 then performs control according to the instruction signal.

For example, when the operator turns on the dissection selection switch 11a, the CPU 45 sends the operation signal to a CPU 56 of the high-frequency output device 4 through the communication cable 17 and causes the CPU 56 to output a sinusoidal, high-frequency output signal as a continuous wave for dissection.

When the operator turns on the coagulation selection switch 11b, the CPU 45 sends the operation signal to the CPU 56 of the high-frequency output device 4 through the communication cable 17 and causes the CPU 56 to output a burst-wave high-frequency output signal having an intermittent waveform for coagulation.

When the operator turns on the operation switch 12, the CPU 45 controls the power supply circuit 44 to turn on an ultrasound drive signal and also causes the CPU 56 of the high-frequency output device 4 through the communication cable 17 to turn on high-frequency output.

In the present embodiment, the operation switch 12 functions as a start switch or a tentative output switch when the operation switch 12 is turned on before a selection switch, namely the dissection selection switch 11a or the coagulation selection switch 11b, is operated. That is, when the operation switch 12 is turned on before a selection switch is operated, ultrasound and high frequency lower than a preset value set for the treatment is outputted.

The high-frequency output device 4 contains a waveform generation circuit 51 for generating a sinusoidal wave and a burst wave. A signal outputted from the waveform generation circuit 51 is inputted into an amplifier 53 through a resonance circuit 52.

The signal amplified by the amplifier 53 is applied to a primary winding of an output transformer 54 and a high-frequency output signal for cauterization is generated at a secondary winding.

One end of the secondary winding of the output transformer 54 is conductively coupled to the horn 27 and other components that form a conducting section in the handpiece 2. The other end of the secondary winding is conductively coupled to the counter electrode plate 6 that has a large contact area that is brought into contact with a patient 40.

The resonance circuit 52 is supplied with a power supply voltage from a voltage-variable power supply circuit 55. The waveform generation circuit 51 and the power supply circuit 55 are controlled by the CPU 56.

The CPU 56 controls an output voltage of the power supply circuit 55 in accordance with a setting operation performed through a setting section 19a of the front panel 19, thereby adjusting the amplitude or other parameter of a high-frequency output signal. In the case of a burst wave, the CPU 56 is also capable of changing amplitudes of multiple sinusoidal waves that form a burst wave to control its crest factor as will be described later.

When the dissection selection switch 11a is turned on by the operator, the CPU 56 (to which the operation signal is transmitted from the CPU 45 through the communication cable 17) causes the waveform generation circuit 51 to output a sinusoidal wave. When the coagulation selection switch 11b is turned on, the CPU 56 causes the waveform generation circuit 51 to output a burst wave.

A display 19b is provided on the front panel 19 for displaying information such as an output value outputted from the CPU 56.

The signal amplified by the amplifier 53 described above is inputted into a current detection circuit 57a and a voltage detection circuit 57b that form a detection circuit 57.

The current detection circuit 57a and the voltage detection circuit 57b detect the signal amplified by the amplifier 53 and convert the signal to DC signals representing effective values. The DC voltage and current values are converted to digital voltage and current by A/D conversion circuits 58a, 58b at predetermined intervals, for example every 10 ms, and the digital voltage and current are inputted in the CPU 56.

The CPU 56 uses the inputted DC voltage and current values to calculate a high-frequency output value. The CPU 56 also calculates the impedance of the high-frequency output.

An ON/OFF signal from the foot switch 5 is also inputted into the CPU 56.

A procedure performed in the surgical system 1 for dissection of an organ 61 such as the liver in the chest of a patient 40 will be described with reference to FIG. 4.

An operator connects the handpiece 2 to the ultrasound drive device 3 and the high-frequency output device 4 as shown in FIG. 1.

Figure 4:
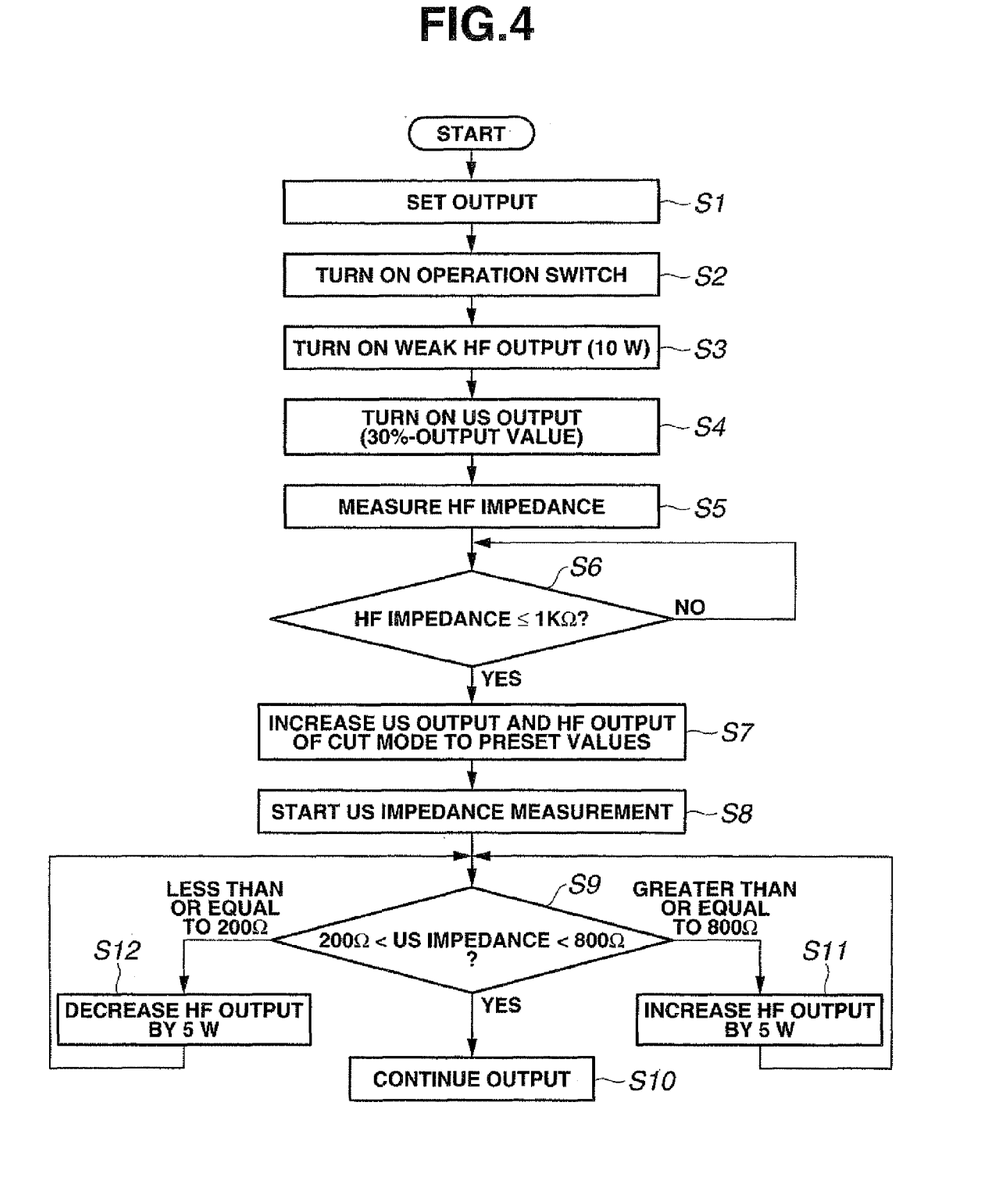
FIG. 4 is a flowchart showing a process of a surgical operation method according to the first embodiment of the present invention.

Then, the operator powers on the ultrasound drive device 3 and the high-frequency output device 4 and sets ultrasound and high-frequency output used for dissection treatment, as shown at step S1 of FIG. 4.

The operator brings the treatment section 9 at the distal end portion of the handpiece 2 inserted in the chest of the patient 40, schematically shown in FIG. 3, close to the organ 61 to be cut. The operator turns on the operation switch for tentatively outputting ultrasound energy and high-frequency energy from the treatment section 9, as shown at step 2 of FIG. 4.

The operation signal is transmitted to the CPU 45 of the ultrasound drive device 3 and is then transmitted from the CPU 45 to the CPU 56 of the high-frequency output device 4.

Then, the CPU 56 turns on a weak high-frequency (abbreviated as HF in FIG. 4) output, for example at 10 W, as shown at step S3.

As shown at step S4, the CPU 45 turns on ultrasound (US in FIG. 4). Here, the output value of the ultrasound is set to a value equivalent to approximately 30% of the output value (set value) set at step S1. That is, after the completion of steps S3 and S4, the handpiece 2 is driven at a tentative value sufficiently smaller than the set value (output value) used for actual dissection treatment with the treatment section 9.

Then, the CPU 56 of the high-frequency output device 4 measures the high-frequency (abbreviated as HF in FIG. 4) impedance, as shown at step S5.

Here, the CPU 56 measures the high-frequency impedance by calculating the high-frequency impedance from voltage and current obtained through the detection circuit 57 at predetermined intervals.

Then at step S6, the CPU 56 determines whether the calculated high-frequency impedance value is less than or equal to 1 kΩ, thereby determining whether the treatment section 9 at the distal end portion of the handpiece 2 is in contact with the organ 61. When the high-frequency impedance value is greater than 1 kΩ, the CPU 56 determines that the treatment section 9 is not in contact with the organ 61, and repeats the operation of step S6.

On the other hand, when the CPU 56 determines that the high-frequency impedance value is less than or equal to 1 kΩ, the CPU 56 determines that the treatment section 9 at the distal end portion of the handpiece 2 is in contact with the organ 61, and proceeds to step S7.

The CPU 56 may measure current and may make determination as to whether the treatment section 9 at the distal end portion of the handpiece 2 is in contact with the organ 61 on the basis of whether the current value is greater than or equal to a predetermined value, instead of performing the operations of steps S5 and S6.

At step S7, the CPU 56 sends the result of the determination made at step S6 to the CPU 45. The CPU 45 receives the result of the determination and increases the ultrasound output to the value set at step S1. The CPU 56 also increases the high-frequency output to the set value in a cut mode (continuous sinusoidal wave).

In this state, the treatment section 9 is in contact with the organ 61 at the site of dissection and the ultrasound energy and high-frequency energy are simultaneously provided from the treatment section 9 to the organ 61. The operator brings the treatment section 9 into contact with the site of dissection in the organ 61 and performs dissection treatment (surgical operation).

When both energies are provided from the treatment section 9 to the organ 61 and the treatment section 9 becomes ready to actually cut, the CPU 45 starts measurement of ultrasound impedance at step S8.

That is, both energies are provided from the treatment section 9 to the organ 61 and measurement (monitoring) of ultrasound impedance corresponding to the state of ultrasound drive by the ultrasound transducer 23 is started in order to monitor the state of dissection.

In particular, the CPU 45 calculates the ultrasound impedance from the voltage and current obtained through the detection circuit 46 at predetermined intervals (for example at intervals of 10 ms).

Then, at step S9, the CPU 45 determines whether the calculated ultrasound (abbreviated as US in FIG. 4) impedance value is within a predetermined range, for example in the range from 200Ω to 800Ω.

When the CPU 45 determines that the calculated ultrasound impedance value is within the predetermined range, the CPU 45 performs control so as to maintain the output state before the determination, as shown at step S10.

On the other hand, when the CPU 45 determines that the calculated ultrasound impedance value is greater than or equal to an upper limit of 800Ω, the CPU 45 performs control to increase the high-frequency output by a predetermined amount (for example 5W), as shown at step S11, then returns to step S9.

When the ultrasound impedance value is greater than or equal to an upper limit of 800Ω, the organ 61 being cut is in a dry state, or is living biological tissue that contains a large amount of fat or the like and is hard in ultrasound terms. Therefore, the high-frequency output is increased by a predetermined amount as shown at step S11, thereby increasing the dissection capability of the treatment section 9. By increasing the high-frequency output, the capability of dissection by the high-frequency energy is increased. The increase also has the effects of increasing the amount of water vapor generated during the high-frequency cauterization treatment and decreasing the ultrasound impedance value at the site being treated with the treatment section 9.

Therefore, when the state in which the region to be cut with the treatment section 9 indicates an ultrasound impedance value greater than or equal to an upper limit of 800Ω, an ultrasound impedance value suitable for dissection treatment with the treatment section 9 can be set by repeating the loop of steps S9 and S11.

When the CPU 45 determines that the ultrasound impedance value is less than or equal to a lower limit of 200Ω, the CPU 45 performs control to decrease the high-frequency output by a predetermined amount (for example 5W) as shown at step S12, then returns to step S9.

As the high-frequency output is decreased, the dissection capability by the high-frequency output decreases and the decrease helps the cut region sufficiently coagulate. The reduction of high-frequency output also has the effects of reducing the amount of water vapor generated by high-frequency cauterization and increasing the ultrasound impedance value in the state in which treatment with the treatment section 9 is being performed.

Thus, ultrasound impedance value suitable for dissection treatment can be set by repeating the loop of steps S9 and S12 during the dissection treatment in which the treatment section 9 is being moved to cut a region to be cut while coagulating the site of dissection.

When the operator performs dissection treatment of a region to be cut by using ultrasound energy and high-frequency energy, the operation described above is performed to monitor the ultrasound impedance in the state of the dissection treatment at predetermined intervals and feedback control is performed to automatically increase or decrease the high-frequency output in response to the monitored ultrasound impedance value, thereby adjusting the high-frequency output so that the high-frequency output falls within an ultrasound impedance range suitable for the dissection treatment.

After the ultrasound impedance value suitable for the treatment is set, the operator can perform the dissection treatment quickly and efficiently by operation at step S10.

In the example of the related art described earlier, acoustic impedance (corresponding to ultrasound impedance) is detected and compared with a threshold to turn on or off high-frequency output. In that case, according to the description of the operations when the detected acoustic impedance exceeds the threshold (because the site cauterized is hardened and the acoustic impedance at the site increases), the high-frequency output is turned off.

In other words, according to the example of the related art, when acoustic impedance exceeds the threshold, it is determined that the site has been cauterized and high-frequency output is turned off to discontinue the high-frequency output.

Therefore, unlike the present embodiment, the example of the related art does not monitor the state of dissection treatment being performed with the treatment section 9 during the period from the start to end of the dissection to control high-frequency output to a value appropriate to the dissection treatment on the basis of the result of the monitoring.

According to the present embodiment, the region of an organ 61 under surgery that is to be cut is cut with the treatment section 9 while the region is being coagulated with the treatment section 9 and the treatment section 9 is moved at a constant speed. The state is monitored during the period from the start to end of the dissection by monitoring ultrasound impedance.

Based on the ultrasound impedance monitored, the high-frequency output value is controlled to a high-frequency output suitable for the treatment, as follows.

Determination is made as to whether the detected ultrasound impedance value is within a predetermined range. When the ultrasound impedance value is out of the predetermined range, control is performed to increase or decrease the high-frequency output by a predetermined amount. The control is repeatedly performed at predetermined intervals in the direction in which the ultrasound impedance value approaches the predetermined range suitable for dissection.

The control significantly differs from that in the example of the related art. When the detected ultrasound impedance value is greater than the upper limit of the predetermined range, control is performed to increase the high-frequency output value by a predetermined amount (the high-frequency output is not turned off).

The present embodiment automatically adjusts the high-frequency output on the basis of ultrasound impedance values detected at intervals so that the ultrasound impedance falls within an ultrasound impedance range suitable for dissection treatment without the need for an operator to manually adjust the high-frequency output so as to fall within the ultrasound impedance range suitable for dissection while the operator is dissecting a region to be cut with the treatment section 9.

Thus, the present embodiment can save the operator the trouble of adjusting the high-frequency output especially during surgery and can improve operability during dissection surgery. Furthermore, dissection treatment can be performed efficiently or easily in a short time.

The embodiment has been described with an operation in which the high-frequency output is placed in the cut mode and dissection is performed in the cut mode. Another method can be chosen in which the high-frequency output is placed in a coagulation mode and dissection is performed in the coagulation mode.

In this method, when a calculated ultrasound impedance is out of a predetermined range, control is performed to increase or decrease the crest factor (peak factor) of a high-frequency output signal waveform, instead of changing a high-frequency output value.

The crest factor is the ratio of peak value to effective value of a high-frequency output signal waveform used. In the cut mode, a high-frequency signal has a continuous sinusoidal waveform and its crest factor is a constant value (1.41).

Figure 5:
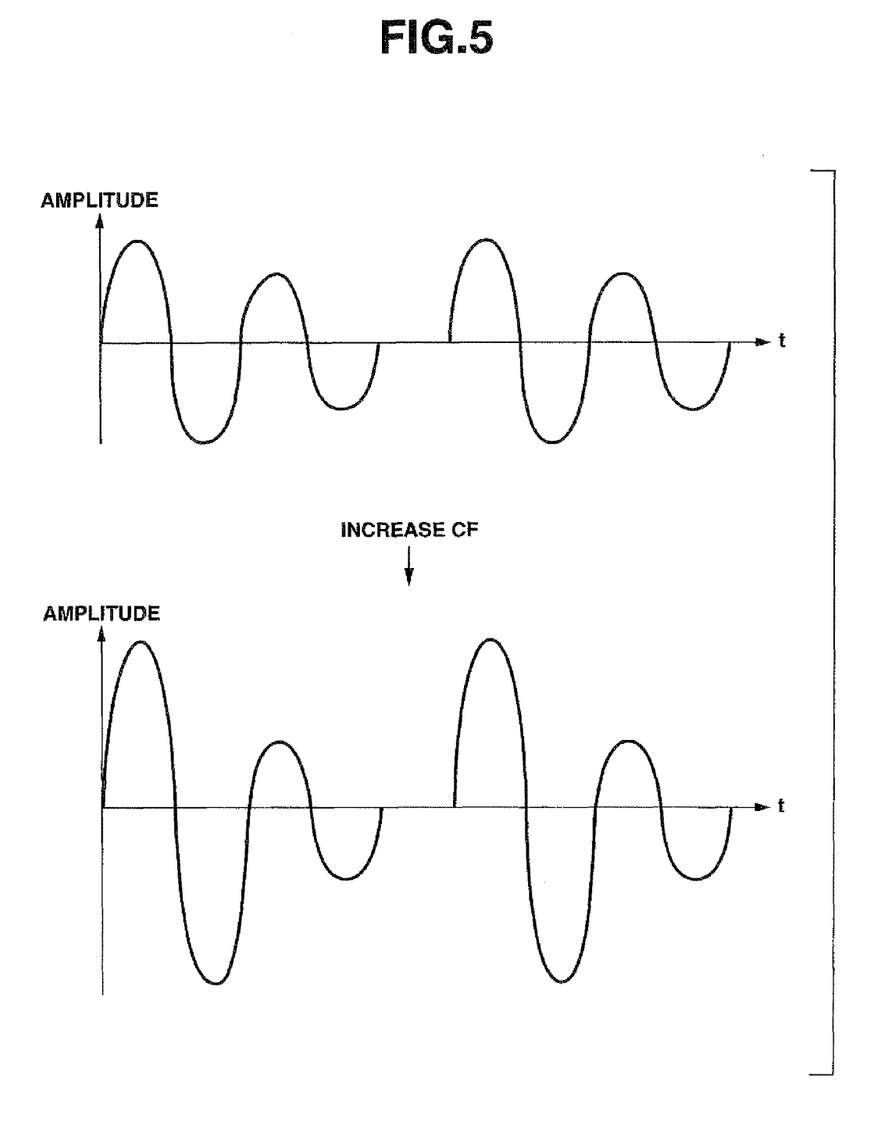
FIG. 5 is a diagram showing a waveform produced by changing a crest factor value of a high-frequency output signal in a coagulation mode.

On the other hand, a burst wave having an intermittent waveform is used in the coagulation mode. FIG. 5 shows an example of the waveform. A waveform with an increased crest factor (the waveform shown in the lower part) is also shown in FIG. 5. The crest factor is increased by processing at step S12' of FIG. 6, which will be described below.

Figure 6:
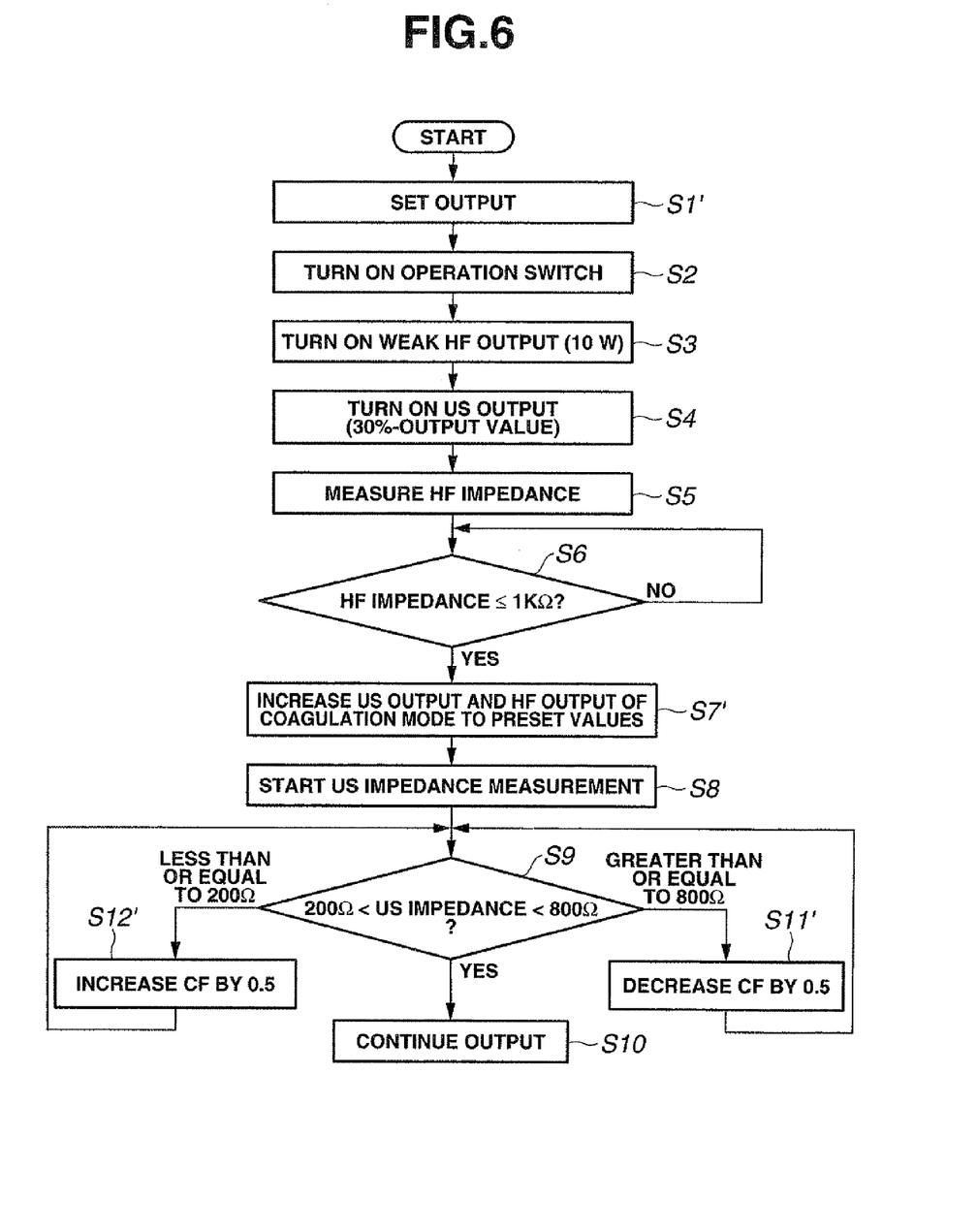
FIG. 6 is a flowchart showing a process of a surgical operation method using a high-frequency output signal in the coagulation mode.

A flowchart in FIG. 6 shows a process performed in the coagulation mode. The process in FIG. 6 is similar to the process in FIG. 4 and therefore only differences from the process in FIG. 4 will be described. The first step S1' of setting output values is the same step S1 of FIG. 4, except that a coagulation mode is selected (set), if a treatment mode to be used is also set.

Steps S2 to S6 are performed in a manner similar to that in FIG. 4. When it is determined at step S6 that a calculated high-frequency impedance value is less than or equal to 1 k$\Omega$, the process proceeds to step S7'. Step S7' differs from step S7 in that a high-frequency output is set in the coagulation mode at step S7', instead of being set in the cut mode as in step S7.

After step S7', steps S8 and S9 are performed in a manner similar to that in FIG. 4. Steps S11' and S12' are performed as shown in FIG. 6, instead of steps S11 and S12 of FIG. 4.

That is, when the calculated ultrasound impedance value is greater than or equal to 800$\Omega$, the CPU 45 reduces the crest factor (abbreviated as CF in FIG. 6) by 0.5 as shown at step S11' and then returns to step S9. Change of the crest factor is performed by sending information indicating the change from the CPU 45 to the CPU 56 to cause the CPU 56 to change the crest factor.

When the calculated ultrasound impedance value is less than or equal to 200$\Omega$, the CPU 45 increases the crest factor by a predetermined amount, for example 0.5, as shown at step S12' and then returns to step S9. An exemplary waveform produced by increasing the crest factor at step S12' is shown in the lower part of FIG. 5.

While changing a crest factor is not equivalent to changing a high-frequency output, changing a crest factor functions in the same way as changing a high-frequency output in the case of dissection treatment in the present embodiment.

Therefore, the method for treatment shown in FIG. 6 has an advantage similar to that described with reference to FIG. 4. Instead of changing the crest factor, the number of waves of intermittent waveform (burst wave) may be changed.

Figure 7:
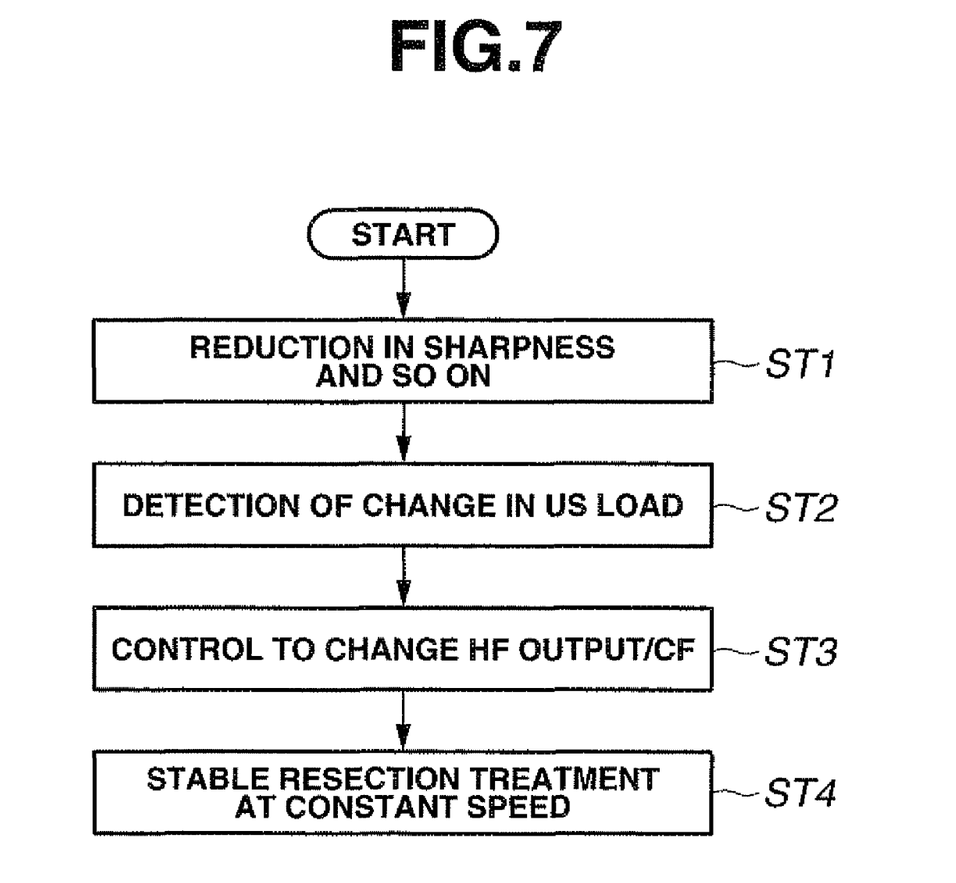
FIG. 7 is a diagram illustrating the operation in FIGS. 4 and 6.

FIG. 7 illustrates the operation shown in FIGS. 4 and 6. An ultrasound output and a high-frequency output are set to preset values as shown at step S7 of FIG. 4 or step S7' of FIG. 6 and treatment for dissection a region to be cut is performed with the handpiece 2 while ultrasound impedance in that state is monitored as shown at step S8.

When cut tissue has been cauterized and stuck or burnt to the treatment section 9 at the distal end portion of the handpiece 2, dissection speed may decrease and the dissection capability of the treatment section 9 may be reduced. On the other hand, if the dissection capability is excessively high (with respect to coagulation), coagulation treatment cannot be sufficiently performed in the sharp dissection state (light load state in this case).

The ultrasound impedance is monitored to detect such a state as a change in ultrasound load as shown at ST2 of FIG. 7.

Control is performed to change the high-frequency output/crest factor in response to a change in the ultrasound load as shown at ST3 of FIG. 7. The control to change the crest factor of an intermittent waveform may be defined in effect as being included in control to the change high-frequency output.

The control at ST3 has the effect of bringing the ultrasound load at ST3 back into an appropriate range. Consequently, the dissection treatment can be performed at a constant speed in a stable manner as shown at ST4.

In this way, the present embodiment can save the operator the trouble of adjusting the high-frequency output and improve operability. The object of saving the trouble of adjusting high-frequency output during dissection treatment is thus achieved.

The operator can perform surgery efficiently in a short time without having to adjust the high-frequency output because the high-frequency output is automatically controlled to a state suitable for dissection treatment.

In the embodiment described above, when a calculated ultrasound impedance is out of a predetermined range, control is performed to increase or decrease a high-frequency output (FIG. 4) or control is performed to increase or decrease the crest factor of a high-frequency output signal waveform (FIG. 6).

In a first variation of the embodiment, control may be performed to change the waveform of a high-frequency output signal, that is, control may be performed to change the waveform of a high-frequency output signal between a continuous waveform and an intermittent waveform (in other words, a cut mode and a coagulation mode) when a calculated ultrasound impedance is out of a predetermined range.

Figure 8:
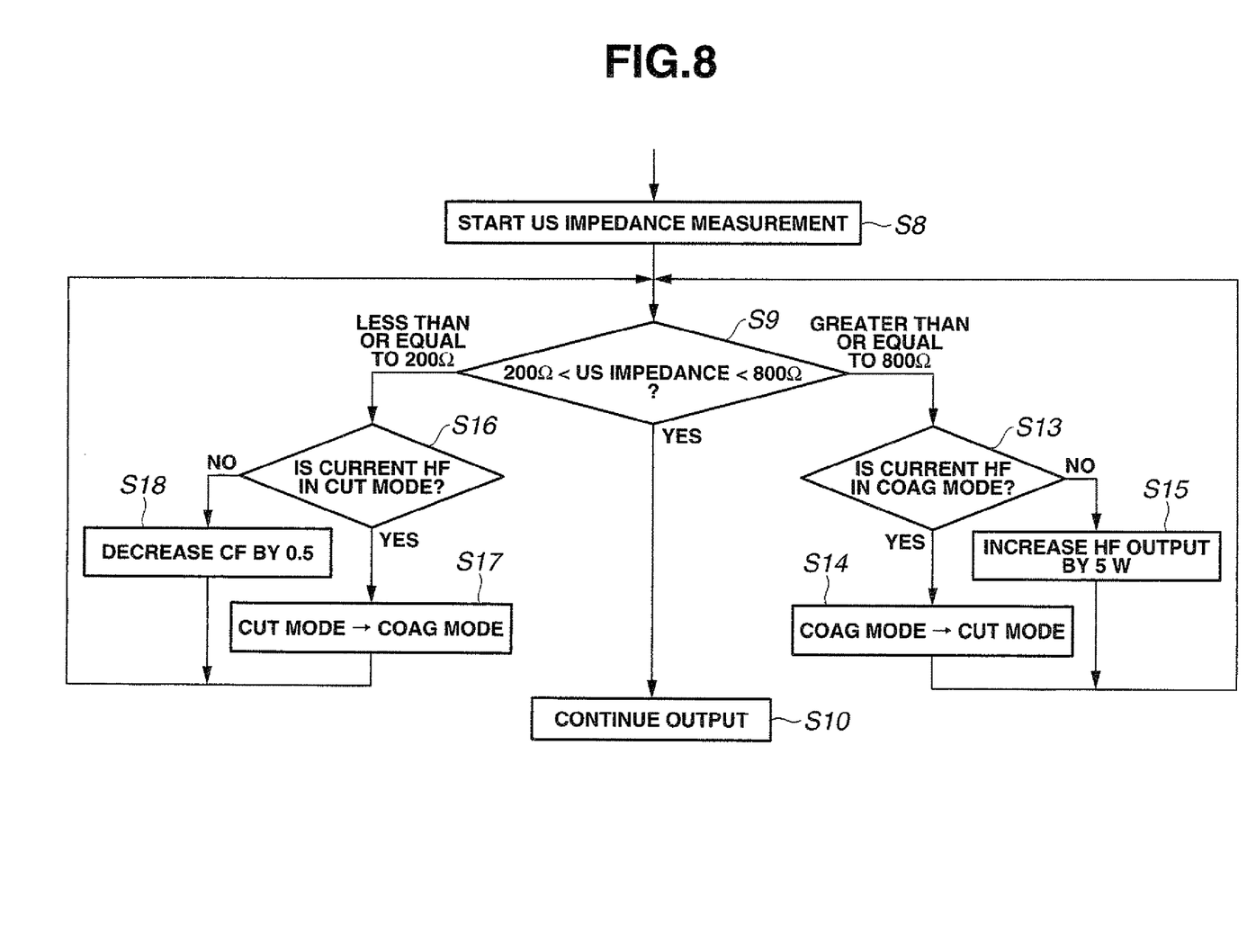
FIG. 8 is a flowchart showing a part of a process in a first variation of the first embodiment.

An operator selects the control through the setting section 18*a*. In this case, the CPU 45 includes a mode change (or waveform change) 45*c* (see FIG. 3) function in addition to the functions of the first embodiment. FIG. 8 shows a process of the variation.

The step 1 to 9 of the process in FIG. 8 are the same as those in FIG. 4, for example. When the CPU 45 determines at step S9 that a calculated ultrasound impedance value is in a predetermined range, the CPU 45 proceeds to step S10 as in the process in FIG. 4.

On the other hand, when the CPU 45 determines at step S9 that the calculated ultrasound impedance value is greater than or a equal to an upper limit of 800$\Omega$, the CPU 45 determines that a load is large and makes determination as to whether the current high-frequency output signal is in a coagulation mode or not, as shown at step S13.

When the signal indicates the coagulation mode, the CPU 45 changes the mode from the coagulation mode to a cut mode (for example with the same output value), as shown at step S14, and then returns to step S9. The mode change is accomplished by sending information indicating the mode change from the CPU 45 to the CPU 56 to cause the CPU 56 to change the mode.

On the other hand, when the signal does not indicates the coagulation mode, that is, indicates the cut mode, the CPU 45 performs control to increase the high-frequency output by a predetermined value (for example 5W) as shown at step S15, and then returns to step S9.

That is, when the CPU 45 determines that the load is large, the CPU 45 changes the mode from the coagulation mode to the cut mode to increase the dissection capability by the high-frequency output signal, or, if the signal indicates the cut mode, increases the high-frequency output.

On the other hand, when the CPU 45 determines at step S9 that the calculated ultrasound impedance value is less than or equal to a lower limit of 200Ω, the CPU 45 determines that the load is small and makes determination as to whether the current high-frequency output signal indicates the cut mode, as shown at step S16.

If the signal indicates the cut mode, the CPU 45 changes the mode from the cut mode to the coagulation mode (with the same output value, for example), as shown at step S17, and then returns to step S9. The mode change is accomplished by sending information indicating the mode change from the CPU 45 to the CPU 56 to cause the CPU 56 to change the mode.

On the other hand, if the current high-frequency output signal does not indicates the cut mode, that is, indicates the coagulation mode, the CPU 45 performs control to decrease the crest factor by a predetermined value (for example 0.5), as shown at step S18, and then returns to step S9.

That is, when the CPU 45 determines that the load is small, the CPU 45 changes the current mode from the cut mode to the coagulation mode to decrease the dissection capability by the high-frequency output signal, or, if in the coagulation mode, decreases the crest factor. The variation has the same advantages as those of the first embodiment.

A second variation of the first embodiment will be described with reference to FIGS. 9 and 10. In the foregoing, when a calculated ultrasound impedance value is out of a predetermined range, control is performed to increase or decrease the value by using a predetermined output value.

In the present variation, when ultrasound impedance value is out of a predetermined range, control is performed to increase or decrease the high-frequency output in accordance with a preset table. In this case, the range of high-frequency output values is also controlled as appropriate to a handpiece 2 actually used.

Figure 9:
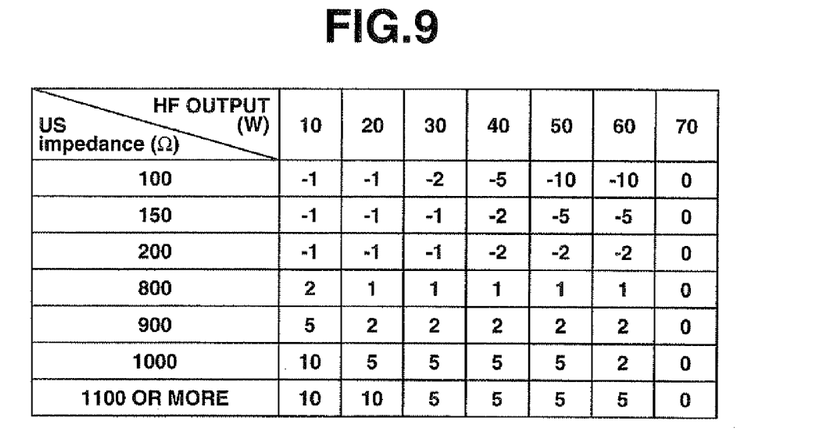
FIG. 9 shows a high-frequency output increment/decrement table in a second variation of the first embodiment.

FIG. 9 shows an exemplary lookup table (LUT) 49a of increments/decrements of high-frequency output stored in a memory 49 beforehand in the present variation. In FIG. 9, the increments/decrements are 0 at ultrasound impedance values in the range between 200Ω inclusive (for example 210Ω) and 800Ω, exclusive, (for example 790Ω) and therefore the increments/decrements in the range are omitted from FIG. 9.

Figure 10:
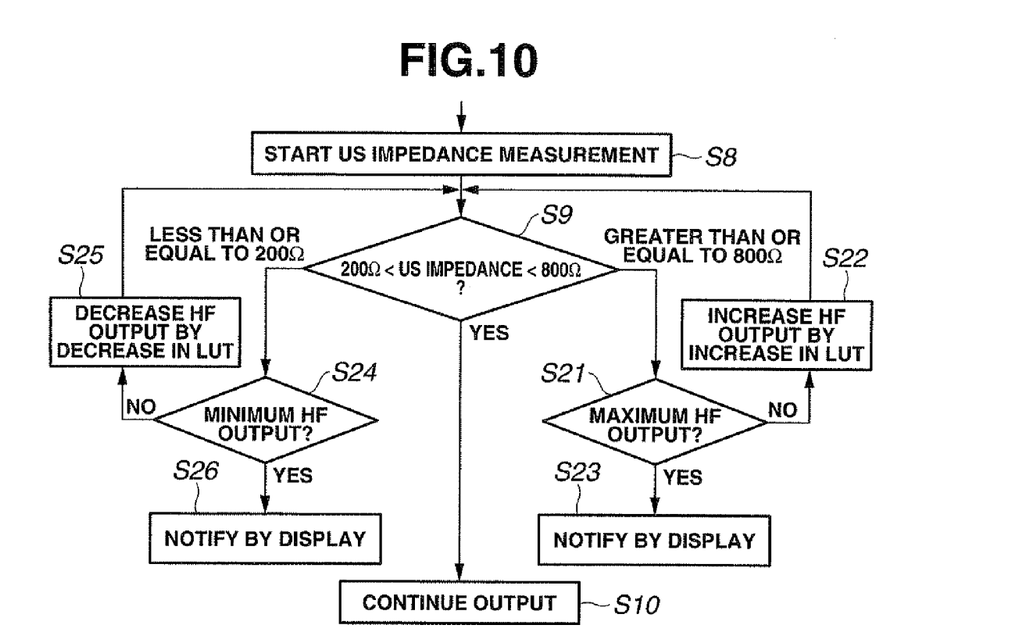
FIG. 10 is a flowchart showing a part of a surgical operation method using the table shown in FIG. 9.

FIG. 10 is a flowchart of a part of a process in a surgical operation method using the LUT 49a shown in FIG. 9. Step S1 to S8 of the process are the same as those in FIG. 4 and therefore the description of which will be omitted.

Ultrasound impedance measurement is started at step S8 of FIG. 10. Then, at step S9, the CPU 45 makes determination as to whether a calculated ultrasound impedance value is within a predetermined impedance range, as in the process in FIG. 4.

When the ultrasound impedance value is in the predetermined impedance range, the process proceeds to step S10, as in the process in FIG. 4.

On the other hand, when it is determined at step S9 that the calculated ultrasound impedance value is greater than the upper limit of the predetermined impedance range, the CPU 45 makes determination as to whether a current high-frequency output value has reached a maximum high-frequency output value, as shown at step S21. When the current high-frequency output value has not reached the maximum high-frequency output value, the CPU 45 refers to the LUT 49a and increases the high-frequency output value by an increment.

That is, the CPU 45 reads from the LUT 49a an increment by which the high-frequency output is to be increased when data represents the current high-frequency output value and ultrasound impedance value, increases the current high-frequency output value by the read increment, and then returns to step S9.

On the other hand, when the current high-frequency output value has reached the maximum high-frequency output value (70 W in FIG. 9), the CPU 45 displays information indicating that the maximum high-frequency output value has been reached on the display 18b to notify the operator, as shown at step S23. The CPU 45 then performs control processing according to an instruction manually inputted by the operator.

When it is determined at step 9 that the calculated ultrasound impedance value is lower than the lower limit of the predetermined impedance range, the CPU 45 determines whether the current high-frequency output value has reached a minimum high-frequency output value, as shown at step S24.

When the current high-frequency output value has not reached the minimum high-frequency output value, the CPU 45 refers to the LUT 49a and decreases the high-frequency output value by a decrement, as shown at step S25.

That is, the CPU 45 reads from the LUT 49a a decrement by which the high-frequency output should be decreased when data represents the current high-frequency output value and ultrasound impedance value, decreases the current high-frequency output value by that decrement, and then returns to step S9.

On the other hand, when the current high-frequency output value has reached the minimum high-frequency output value (0 W in FIG. 9), the CPU 45 displays information indicating the fact to notify the operator, as shown at step S26. The CPU 45 then performs control processing according to an instruction manually inputted by the operator.

According to the present variation, increments and decrements by which high-frequency output values should be increased or decreased are provided beforehand for different set values of high-frequency output values or different ultrasound impedance values including those of a target region of patient's body. Consequently, dissection treatment can be performed more appropriately and efficiently.

The LUT 49a may be implemented by a rewritable nonvolatile memory such as a flash memory so that past treatment data stored is updated with more desirable increment/decrement table data.

In the present variation, a method is used in which, when a calculated ultrasound impedance value is out of a predetermined range, increments and decrements of high-frequency output stored beforehand in the LUT 49a are referenced to determine an increment or decrement. However, an operator may be allowed to select or determine an increment or decrement by setting the increment or decrement through the setting section 18a or other means.

Furthermore, when a coagulation mode is set as the mode of treatment by a high-frequency output signal, a table of increments and decrements by which a crest factor is to be increased or decreased when a calculated ultrasound impedance value is out of a predetermined range may be provided beforehand.

Second Embodiment

A second embodiment of the present invention will be described with reference to FIGS. 11 and 12. An object of the present embodiment is the same as that of the first embodiment.

Figure 11:
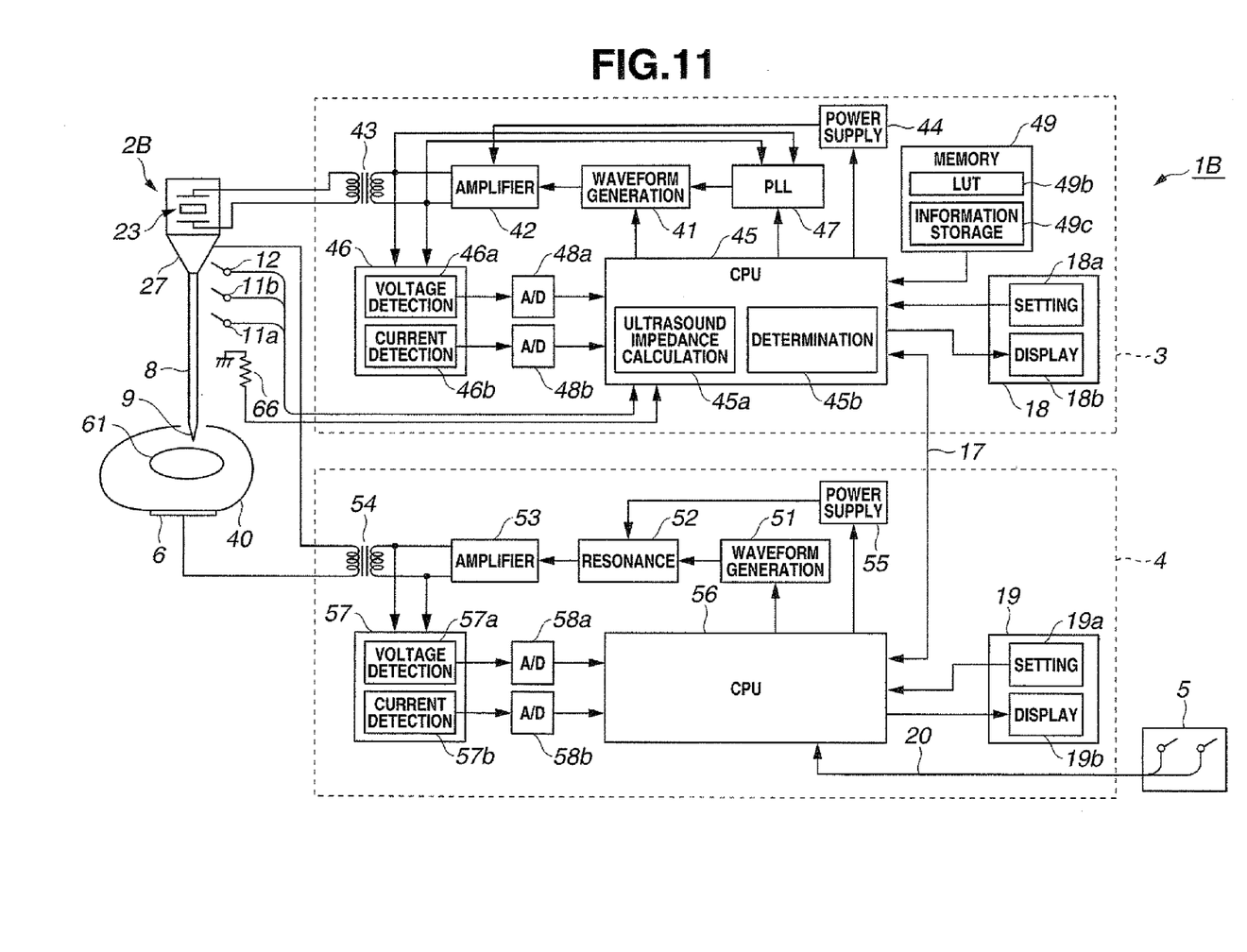
FIG. 11 is a perspective view showing a general configuration of a surgical system according to a second embodiment of the present invention.

FIG. 11 shows a configuration of a surgical system 1B according to the second embodiment of the present invention. In the surgical system 1B, any of multiple handpieces 2B of different types having different characteristics can be detachably connected to an ultrasound drive device 3 which is equivalent to the ultrasound drive device 3 of the surgical system 1 in FIG. 3.

Each of the handpieces 2B has type information generating means, which may be a resistance 66, for example, for generating information indicating the type of the handpiece 2B, in addition to the components of the handpiece 2 shown in FIG. 3.

A CPU 45 in the ultrasound drive device 3 identifies the type of the handpiece 23 connected to the ultrasound drive device 3 from a resistance value of the resistance 66 or a predetermined voltage divided by the resistance 66. Instead of type information generating means, which may be the resistance 66, for example, a type information field of ID information unique to each handpiece 2B may be used.

A LUT 49b containing tables of increments and decrements of high-frequency output associated with the types of handpieces 21B is stored in a memory 49. That is, the LUT 49b includes LUTs 49a as many as the number of types of handpieces 2B, each for one type.

The CPU 45 can use an increment/decrement table associated with a handpiece 2B of the type identified from the LUT 49b to perform an operation similar to that described with respect to the variations of the first embodiment.

Figure 12:
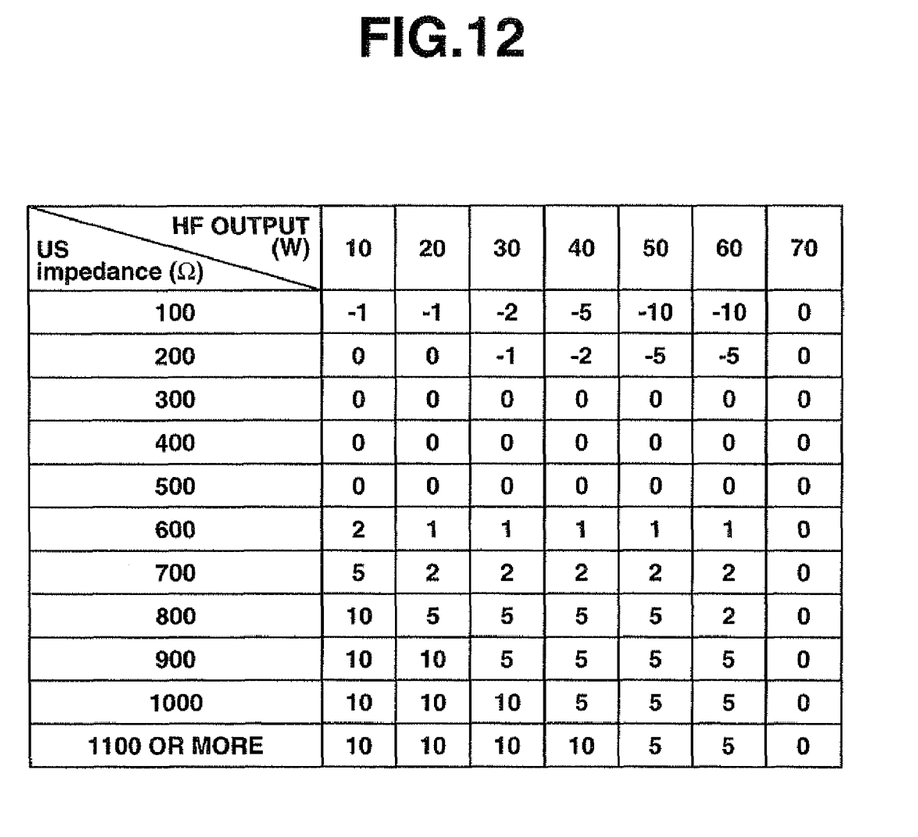
FIG. 12 is a diagram showing an exemplary high-frequency output increment/decrement table in the second embodiment.

For example, FIG. 12 shows an exemplary increment/decrement table of the LUT 49b for a handpiece of a type different from the handpiece 2 used in the first embodiment. The table differs from the table shown in FIG. 9 in predetermined ranges, for example.

According to the present embodiment, dissection treatment appropriate to a handpiece 2B among handpieces 2B of different types can be performed quickly and efficiently.

Furthermore, in the present embodiment, information indicating an ultrasound impedance ranges suitable for each target organ or region to be cut, for example information including values from the lower to upper limits of an ultrasound impedance range, is associated with the organ or region and stored beforehand in an information storage area 49c of a memory 49, for example.

When an operator selects or inputs the liver, for example, as the organ or region to be cut through the use of a setting section 18a, the CPU 45 receives the input and reads information indicating the ultrasound impedance range associated with the liver from the information storage area 49c.

The information indicating the ultrasound impedance range here may include information indicating the ultrasound impedance range from a lower limit of 200Ω to an upper limit of 800Ω, for example.

The CPU 45 then displays the information on a display 18b and prompts the operator to confirm whether the operator wants to use the information for the treatment. When the operator confirms the use of the information, the CPU 45 uses the information to control the high-frequency output.

According to the present embodiment, appropriate treatment can be easily performed on an organ to be cut even when the organ has different ultrasound characteristics, because information indicating different ultrasound impedance ranges suitable for different regions to be cut is stored beforehand as described above. In addition, ease of use for the operator can be improved.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A surgical system comprising:
a surgical instrument including a conducting section transmitting ultrasound vibration generated by an ultrasound transducer to a distal end portion that functions as a treatment section and transmitting a high-frequency output signal to the distal end portion;
an ultrasound drive section outputting an ultrasound drive signal for driving the ultrasound transducer;
a high-frequency output section outputting a high-frequency output signal to the conducting section;
a detection section detecting an ultrasound impedance corresponding to an ultrasound drive state of the distal end portion in a state in which ultrasound energy is provided from the distal end portion to a site of surgery;
a determination section determining whether the ultrasound impedance value detected by the detection section is within a predetermined range;
an information storage section having a lookup table storing an increment or a decrement of a predetermined high-frequency output value based on the ultrasound impedance value detected by the detection section; and
a control section
performing control to maintain the high-frequency output value when the determination section determines that the ultrasound impedance value is within the predetermined range,
reading out the increment or the decrement corresponding to the ultrasound impedance value from the lookup table when the determination section determines that the ultrasound impedance value is out of the predetermined range, and
performing control to increase the high-frequency output value by the corresponding increment when the determination section determines that the ultrasound impedance value is greater than an upper limit of the predetermined range, and performing control to decrease the high-frequency output value by the corresponding decrement when the determination section determines that the ultrasound impedance value is less than a lower limit of the predetermined range.

2. The surgical system according to claim 1, wherein the determination section determines whether a detected ultrasound impedance value is in a range between a lower limit and an upper limit that are two boundary values of the predetermined range.

3. The surgical system according to claim 1, wherein the control section repeats, at predetermined intervals, continuous output control to increase, decrease, or maintain the high-frequency output value in accordance with the determination by the determination section.

4. The surgical system according to claim 1, wherein the increment and the decrement are less than or equal to 10 W.

5. The surgical system according to claim 1, further comprising an information storage section in which information indicating the predetermined range is stored beforehand associated with a plurality of different sites of surgery.

6. The surgical system according to claim 1, wherein, if the high-frequency output signal has an intermittent waveform, the control section performs control to change a crest factor of the intermittent waveform when it is determined that the ultrasound impedance value is out of the predetermined range.

7. The surgical system according to claim 1, wherein the control section includes a waveform change section changing a waveform of the high-frequency output signal to a continuous waveform or an intermittent waveform in accordance with the determination by the determination section.

8. The surgical system according to claim 1, wherein in the information storage section, information indicating the predetermined range is stored beforehand associated with a plurality of different sites of surgery.

9. The surgical system according to claim 1, wherein the lookup table stored an increment or a decrement of a crest factor predetermined according to the high-frequency output value and the ultrasound impedance value, and if the high-frequency output signal has an intermittent waveform, the control section reads out the increment or the decrement of the crest factor corresponding to the high-frequency output value and the ultrasound impedance value from the lookup table, and performs control to increase or decrease the crest factor of the intermittent waveform by the corresponding increment or the corresponding decrement of the crest factor, when it is determined that the ultrasound impedance value is out of the predetermined range.

10. The surgical system according to claim 1, wherein the upper limit is 800Ω and the lower limit is 200Ω.

11. A surgical operation method for performing a surgical operation by using a surgical instrument including a conducting section transmitting ultrasound vibration generated by an ultrasound transducer to a distal end portion that functions as a treatment section and transmitting a high-frequency output signal to the distal end portion, the method comprising the steps of:
    detecting an ultrasound impedance corresponding to an ultrasound drive state of the distal end portion in a state in which ultrasound energy is provided from the distal end portion to a site of surgery by driving the ultrasound transducer by an ultrasound drive signal and by outputting a high-frequency output signal to the conducting section;
    determining whether an ultrasound impedance value detected by the step of detecting is in a predetermined range; and
    controlling to
        maintain the high-frequency output value when the step of determining determines that the ultrasound impedance value is within the predetermined range,
        read out, from a lookup table storing an increment or a decrement of a predetermined high-frequency output value according to the ultrasound impedance value detected by the step of detecting, the increment or the decrement corresponding to the ultrasound impedance value when the step of determining determines that the ultrasound impedance value is out of the predetermined range, and
        perform control to increase the high-frequency output value by the corresponding increment when the step of determining determines that the ultrasound impedance value is greater than an upper limit of the predetermined range, and perform control to decrease the high-frequency output value by the corresponding decrement when the step of determining determines that the ultrasound impedance value is less than a lower limit of the predetermined range.

12. The surgical operation method according to claim 11, wherein the step of determining determines whether the ultrasound impedance value is in a range between a lower limit and an upper limit that are two boundary values of the predetermined range.

13. The surgical operation method according to claim 11, wherein the step of controlling repeats, at predetermined intervals, continuous output control to increase, decrease, or maintain the high-frequency output value in accordance with the determination at the step of determining.

14. The surgical operation method according to claim 11, further comprising, as an initial step before the step of detecting, the step of setting output values of the ultrasound drive signal and the high-frequency output signal to tentative output values smaller than set values used for treatment, when the ultrasound transducer is driven by the ultrasound drive signal and the high-frequency output signal is outputted to the conducting section.

15. The surgical operation method according to claim 11, wherein, if the high-frequency output signal has an intermittent waveform, the step of controlling performs control to increase or decrease a crest factor of the high-frequency output signal when it is determined that the ultrasound impedance value is out of a predetermined range.

16. The surgical operation method according to claim 11, wherein, if the high-frequency output signal has an intermittent waveform, the step of controlling maintains the high-frequency output value when it is determined that the ultrasound impedance value is in a predetermined range, performs control to increase a crest factor of the high-frequency output signal by a predetermined amount when it is determined that the ultrasound impedance value is greater than an upper limit of a predetermined range, and performs control to decrease a crest factor of the high-frequency output signal by a predetermined amount when it is determined that the ultrasound impedance value is less than a lower limit of the predetermined range.

17. The surgical operation method according to claim 11, wherein the step of controlling maintains the high-frequency output value when it is determined that the ultrasound impedance value is in a predetermined range, performs control to change the waveform of the high-frequency output signal to a continuous waveform when the ultrasound impedance value is greater than an upper limit of a predetermined range if the waveform of the high-frequency output signal is an intermittent waveform, and performs control to change the waveform of the high-frequency output signal to an intermittent waveform when the ultrasound impedance value is smaller than a lower limit of the predetermined range if the waveform of the high-frequency output signal has a continuous waveform.

18. The surgical system according to claim 11, wherein the upper limit is 800Ω and the lower limit is 200Ω.

* * * * *